(12) United States Patent
Mainster et al.

(10) Patent No.: US 7,278,737 B2
(45) Date of Patent: Oct. 9, 2007

(54) OPHTHALMIC DEVICES HAVING A HIGHLY SELECTIVE VIOLET LIGHT TRANSMISSIVE FILTER AND RELATED METHODS

(75) Inventors: Martin A. Mainster, Leawood, KS (US); Alan J. Lang, Long Beach, CA (US); Michael D. Lowery, Vista, CA (US); Jason Clay Pearson, Kingsport, TN (US); Max Allen Weaver, Kingsport, TN (US); Jean Carroll Fleischer, Kingsport, TN (US); Gregory Alan King, Mount Carmel, TN (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 204 days.

(21) Appl. No.: 11/115,743

(22) Filed: Apr. 26, 2005

(65) Prior Publication Data

US 2005/0243272 A1 Nov. 3, 2005

Related U.S. Application Data

(60) Provisional application No. 60/567,281, filed on Apr. 30, 2004.

(51) Int. Cl.
*G02C 7/10* (2006.01)

(52) U.S. Cl. .................................... 351/162; 351/163
(58) Field of Classification Search ................ 351/162, 351/263, 164, 165, 163
See application file for complete search history.

(56) References Cited

U.S. PATENT DOCUMENTS

| | | | |
|---|---|---|---|
| 4,528,311 A | | 7/1985 | Beard et al. |
| 4,681,412 A | | 7/1987 | Lemelson |
| 4,998,817 A | * | 3/1991 | Zeltzer ........................ 351/162 |
| 5,172,256 A | * | 12/1992 | Sethofer et al. .............. 349/14 |
| 5,235,358 A | | 8/1993 | Mutzhas et al. |
| 5,534,041 A | * | 7/1996 | Havens et al. ............... 35/30.1 |
| 5,866,635 A | | 2/1999 | Collins et al. |
| 6,432,137 B1 | | 8/2002 | Nanushyan et al. |

FOREIGN PATENT DOCUMENTS

WO    WO88/02871    4/1988

\* cited by examiner

*Primary Examiner*—Scott J. Sugarman

(57) ABSTRACT

Ophthalmic devices are provided having a violet-light vertical cut-off filter abruptly absorbs light between the wave lengths of between approximately and 400 nm and 450 nm such that a curve when plotted as percent transmission versus wavelength has the shape as depicted in FIG. 2. In one embodiment the ophthalmic devices are made from acrylates and the light absorbing compound is an Eastman Yellow 035 MA dye.

12 Claims, 5 Drawing Sheets

OPHTHALMIC DEVICES HAVING A HIGHLY SELECTIVE VIOLET LIGHT TRANSMISSIVE FILTER AND RELATED METHODS

CROSS REFERENCE TO RELATED APPLICATIONS

This application claims the benefit of U.S. Provisional Application No. 60/567,281, filed Apr. 30, 2004, which is incorporated herein by reference in its entirety.

FIELD OF THE INVENTION

The present invention relates to ophthalmic devices suitable for use in mammals. More specifically, the present invention relates to ophthalmic devices having at least one highly selective (abrupt) violet light transmissive filter incorporated therein. Additionally, related methods for making ophthalmic devices having highly selective violet light transmissive filters are provided.

BACKGROUND OF THE INVENTION

There are three primary structures within the human eye that are essential to vision and subject to age-related damage: the cornea, lens and retina. The retina is a multi-layered sensory tissue that lines the back of the eye. It contains millions of photoreceptors that capture light rays and convert them into electrical impulses. These impulses travel along the optic nerve to the brain where they are turned into images. There are two types of photoreceptors in the retina: rods and cones. The retina contains approximately 6 million cones. The cones are contained in the macula, the portion of the retina responsible for central vision. They are most densely packed within the fovea, the very center portion of the macula. Cones function best in bright light and allow us to appreciate color. There are approximately 125 million rods. They are spread throughout the peripheral retina and function best in dim lighting. The rods are responsible for peripheral and night vision. The retina is essential for vision and is easily damaged by prolonged unprotected exposure to visible and near visible light. Light-induced retinal pathologies include cystoid macular oedema, solar retinopathy, ocular melanomas and age-related macular degeneration (ARMD). Light-induced retinal damage is classified as structural, thermal or photochemical and is largely determined by the exposure time, power level and wavelength of light (W. T. Ham. 1983. Journal of Occupational Medicine. 25:2 101-102).

In healthy adults the retina is generally protected from the most severe forms of light-induced damage by the outer eye structures including the cornea and crystalline lens. The cornea is a transparent proteinaceous ocular tissue located before the iris and is the only eye structure exposed directly to the environment. The cornea is essential for protecting the delicate internal structures from damage and facilities the transmission of light through the aqueous media to the crystalline lens. The cornea is the primary light filter and therefore is particularly susceptible to excessive light exposure-related damage including corneo-conjunctival diseases such as pterygium, droplet climatic keratopathy and pinguecula. In the healthy eye, the cornea, in conjunction with the aqueous medium, absorbs, or blocks, wavelengths (nm shall be used hereinafter to denote wavelengths of light in nanometers) in the short ultraviolet (UV)-B and UV-C region (less than ≈320 nm).

The crystalline lens is an accommodating biological lens lying directly behind the iris and cornea and facilitates the convergence of both far and near images onto the retina. The natural crystalline lens blocks near UV radiation (UV-A) (320 nm to 400 nm) from reaching the retina. Therefore, most of the damaging UV-A, -B and -C radiation are prevented from reaching the retina in healthy people with an intact crystalline lens and cornea. Thus in the normal mammalian eye only wavelengths between about 400 nm and 1,400 nm can reach the retina. However, high transmittance levels of blue and violet light (wavelengths from about 390 nm to about 500 nm) has been linked to retinal damage, macular degeneration, retinitis pigmentosa, and night blindness. In addition, blue and violet light tends to be scattered in the atmosphere, especially in haze, fog, rain, and snow, which in part can cause glare, and diminished visual acuity. As the eye ages the crystalline lens begins to take on a yellow tint that absorbs some radiation in the blue and violet wavelength ranges, in addition to the majority of near UV radiation. Thus, the natural crystalline lens protects the eye's delicate retina from near UV light throughout life and subtly yellows with age, thereby increasing the amount of blue and violet light that is absorbed.

The natural crystalline lens is also susceptible to age-related degenerative eye diseases such as cataracts. Cataract is a clouding of the crystalline lens caused by the coagulation of lens proteins within the capsular sac. Many ophthalmologists believe that cataract formation results from a lifetime of oxidative insults to the lens and is exacerbated by smoking, excessive exposure to bight light, obesity and diabetes. Cataracts develop slowly in most people and eventually reach the point where vision is substantially impaired resulting in near to total blindness. In these persons lens removal and replacement with synthetic polymer ophthalmic devices such as an intraocular lens is the preferred means for restoring normal sight. However, once the natural crystalline lens is removed the retina is left unprotected from damaging UV and short wavelength violet light. Thus early synthetic ophthalmic devices were provided with UV absorbing compounds such as benzophenones and benzotriazoles-based UV light absorbers. Moreover, many benzophenones and benzotriazoles are polymerizable and thus can be stably integrated into most modern ophthalmic device compositions including acrylates and hydrophilic hydrogel co-monomers and co-polymers. Ultraviolet light does not play a positive role in human vision. Thus ophthalmic devices having UV absorbing dye concentrations that block virtually all UV light became common-place by the mid 1980s.

In the 1990s ophthalmic devices having violet light absorbing materials such as azo dyes incorporated therein were introduced to approximate the violet light blocking effects of the aging adult natural crystalline lens. For example, U.S. Pat. No. 4,390,676, describes polymethylmethacrylate (PMMA) polymer ophthalmic devices incorporating yellow dyes that selectively absorb UV, violet and blue light radiation up to approximately 450 nm. U.S. Pat. Nos. 5,528,322; 5,543,504; and 5,662,707 are assigned to Alcon Laboratories, Inc. and disclose acrylic-functionalized yellow azo dyes having an inert chemical spacer between the dye and acrylic portions of the molecule. Thus the violet light-absorbing portion of the molecule is protected from undesirable color shifts when polymerized with the lens polymer. Moreover, because the dye is acrylic-functionalized, it is polymerizable with the lens polymer and thus stably incorporated into the ophthalmic device polymer matrix. Similarly, Menicon Co., Ltd. holds U.S. Pat. Nos.

6,277,940 and 6,326,448 both disclosing specific acrylic-modified azo dyes structurally similar to Alcon's. Hoya Corporation owns U.S. Pat. No. 5,374,663 that discloses non-covalently linked yellow dyes including solvent yellow numbers 16, 29 and others incorporated into a PMMA matrix. Moreover, Hoya also owns U.S. Pat. No. 6,310,215 that discloses acrylic-functionalized pyrazolone dyes suitable for use in acrylic and silicone ophthalmic devices.

However, these and other prior art ophthalmic devices have the violet blocking dyes evenly distributed throughout the ophthalmic device material at concentrations that simulate the natural yellow color of the 53 year-old individual's crystalline lens. Consequently, all light and images are filtered through a yellow color before being projected on the retina. For activities that rely on acute photopic sensitivity (day light visual conditions) this may be desirable. For example, people who engage in certain day time outdoor sports or activities including skiers, baseball players, football players, pilots, and boaters are exposed to high levels of ultraviolet, violet, and visible light radiation which can affect visual acuity required in such activities. Drivers of motor vehicles also have specific needs in terms of reducing glare and enhancing visual acuity under bright, sunlit driving conditions and reducing headlight glare at night.

However, unlike UV radiation, the violet light spectrum (440 nm to about 500 nm) are important for maintaining optimal visual acuity, especially scotopic (night) vision. Thus ophthalmic devices containing dyes that block significant amounts of violet light over the majority of the violet light spectrum can adversely affect scotopic vision. This is an especially acute problem in older adults that naturally suffer declining scotopic vision and reduced pupil dilation. Consequently, an ophthalmic device is needed that balances the need for reducing the possible damaging effects of blue and violet light exposure against the need to maintain good scotopic vision.

Therefore, it is an objective of the present invention to provide an ophthalmic device having a highly selective (abrupt) violet light transmissive filter incorporated therein that protects against radiation in the violet waveband and more damaging portions of the blue waveband, thus providing improved scotopic vision when compared to prior art devices.

SUMMARY OF THE INVENTION

The present invention achieves this and other objectives by providing an ophthalmic device having a violet light absorbing dye that selectively filters wavelengths between approximately 400 nm to about 450 nm with little or no absorption of wavelengths above 450 nm (referred to herein after as a "violet-light vertical cut-off filter").

The ophthalmic devices of the present invention may be composed of any biocompatible polymer suitable for use in forming an ophthalmic device. For example, but not limited to, poly(methylmethacrylate) (PMMA). Additional polymers may be used when made using monomers selected from the non-limiting group consisting of phenylethylacrylate (PEA), phenylethylmethacrylate (PEMA), methylphenylacrylates, methylphenylmethacrylates, 2-hydroxyethyl methacrylate (HEMA). Moreover, heterocyclic N-vinyl compounds containing a carbonyl functionality adjacent to the nitrogen in the ring, and particular N-vinyl lactams such as N-vinyl pyrrolidone are also suitable for use in accordance with the teachings of the present invention. Moreover, the ophthalmic devices of the present invention may also be cross-linked using di- or multi-functional monomers and in small amounts as is well known in the art. Representative crosslinking agents include ethylene glycol dimethacrylate, triethylene, glycol dimethacrylate and trimethylolpropane trimethacrylate. The cross linking agents are typically dimethacrylates or diacrylates, although dimethacrylamides are also known.

The light absorbing dye used to form the violet-light vertical cut-off filter may be any dye capable of absorbing light between approximately 400 nm to about 450 nm. Exemplary light absorbing dyes include, but not limited to, dyes available from Eastman Chemical such as, but not limited to, Eastman Yellow 035-MA. This dye is a methine class dye and is easily provided with a polymerizable methacrylate group. The absorption spectrum for Yellow 035-MA is provided in FIG. 3. This dye is particularly beneficial because it is a reactive dye that can be chemically bonded to the ophthalmic device polymer so that the lens is colorfast and the dye is non-extractable (i.e. will not bleed or leach out of the lens). However, it is not essential that the dye be polymerizable or capable of bonding to the ophthalmic device polymer. For example, other dyes may also be used in accordance with the teachings of the present invention capable of absorbing the desired wavelength of light.

Other embodiments of the present invention include lenses having additional light absorbing dyes, specifically dyes that absorb light in the ultraviolet region, for example, but not limited to benzophenones and benzotriazoles. In yet other embodiments, the ophthalmic device is a filter only and does not itself have any significant optical power.

In another embodiment of the present invention an ophthalmic device is a lens suitable for implantation into the eye of a mammal such as an intraocular lens or corneal implant wherein the lens comprises a violet-light vertical cut-off filter, and wherein the violet-light vertical cut-off filter may be distributed throughout substantially the entire ophthalmic device or may be distributed through less than the entire ophthalmic device (see FIG. 6). In the latter embodiment of the present invention, the ophthalmic device has a defined region that comprises at least one light absorbing dye, specifically dyes that absorb visible light in the wavelengths between approximately 400 nm and 450 nm. This embodiment is more fully described in co-pending U.S. utility patent application Ser. No. 11/027,876, filed Dec. 29, 2004, which is incorporated herein by reference in its entirety and which claims priority to provisional application Ser. No. 60/533,623, filed Dec. 30, 2003.

The ophthalmic devices made in accordance with the teachings of the present invention include, without limitation, intraocular lenses, corneal implants, sun glasses, spectacles and contact lenses.

Thus, the present invention provides an ophthalmic device that affords enhanced retina protection in high intensity lighting conditions when protection is needed most, while permitting a fuller spectrum of light to reach the retina in subdued, or low light conditions thus enhancing visual acuity and color perception.

BRIEF DESCRIPTION OF THE FIGURES

This patent or application file contains at least one drawing executed in color. Copies of this patent or patent application publication with color drawing(s) will be provided by the Office upon request and payment of the necessary fee.

DEFINITION OF TERMS

"Diopter:" A unit of measurement of the refractive power of lenses equal to the reciprocal of the focal length measured in meters.

Figure 2:
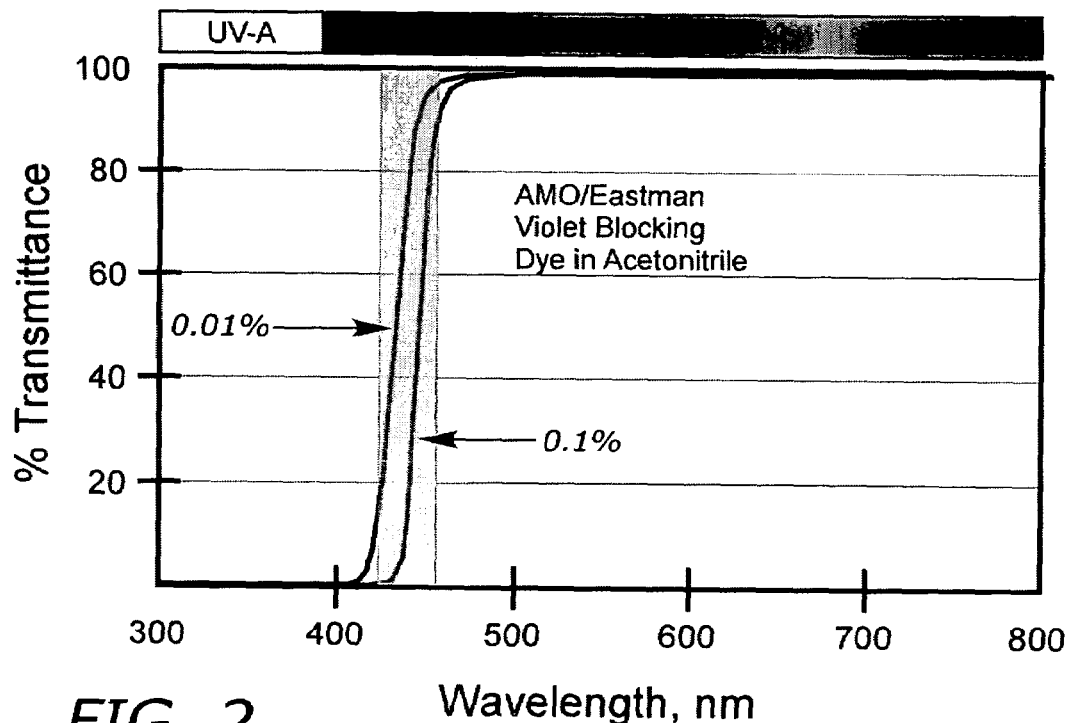
FIG. 2 graphically depicts visible light transmittance curves of an ophthalmic device containing dye filters within the target filter area depicted in FIG. 1.

"Violet-light vertical cut-off filter:" As used herein "Violet-light vertical cut-off filter" shall mean a light absorbing composition that abruptly absorbs light between the wave lengths of between approximately and 400 nm and 450 nm (see FIG. 2). As used herein "abruptly means that the resulting absorption curve (when plotted in percent transmittance versus wavelength in nm) is nearly vertical having the overall shape as depicted in the FIGS. 2 (within the yellow zone) and 4 (red).

"Ophthalmic device(s)" as used herein include without limitation intraocular lenses, sun glasses, spectacles and contact lenses.

DETAILED DESCRIPTION

In certain embodiments the present invention comprises ophthalmic devices having a violet-light vertical cut-off filter incorporated therein wherein the violet-light vertical cut-off filter abruptly absorbs light between the wavelengths of approximately and 400 nm and 450 nm (see FIG. 2).

Figure 3:
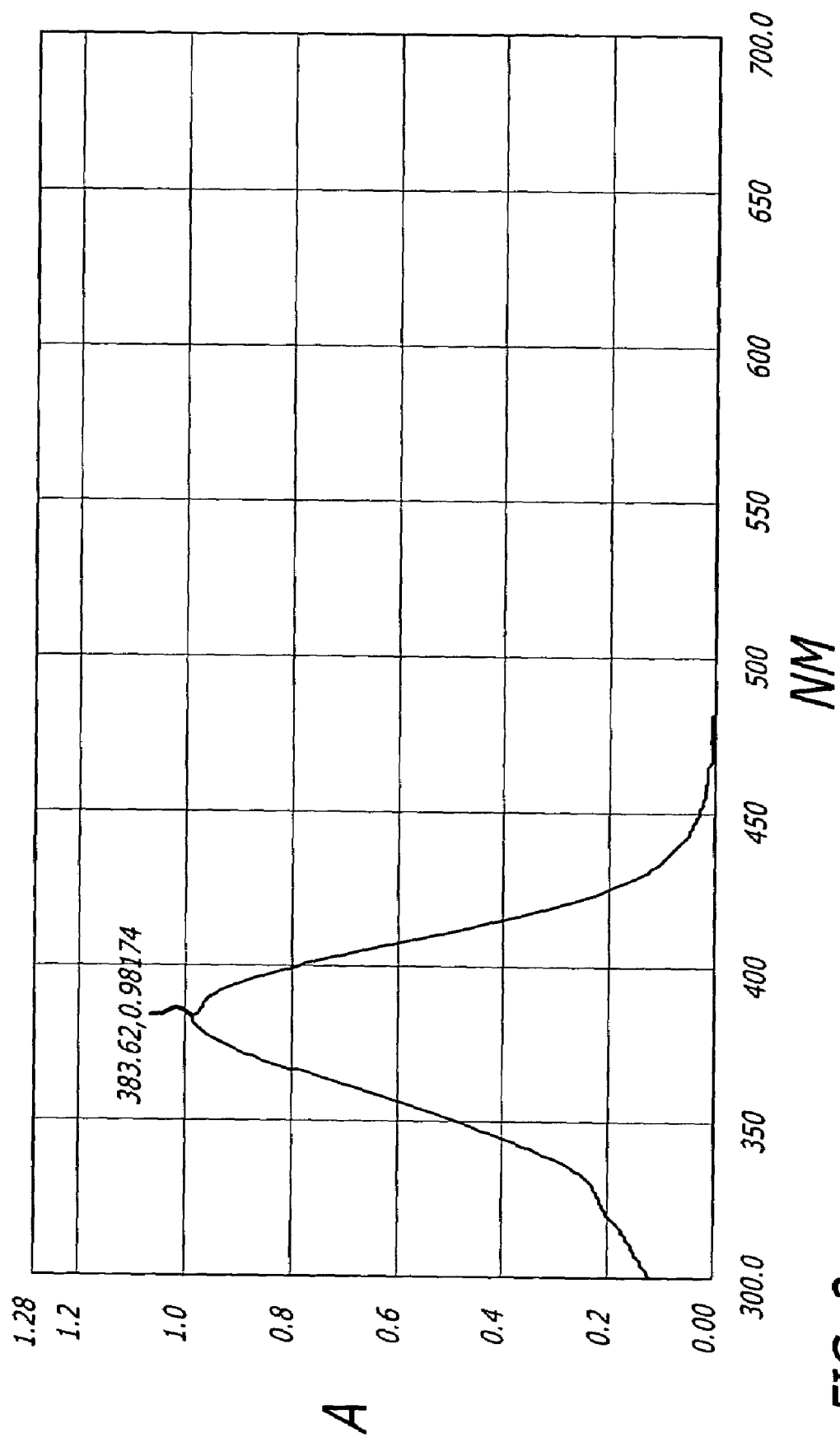
FIG. 3 graphically depicts absorption spectrum for Yellow 035-MA in accordance with the teachings of the present invention.

The light absorbing dye used to form the violet-light vertical cut-off filter can be any dye capable of absorbing light of predetermined wavelengths within the visible light spectrum. Specifically, the dye used in accordance with the teachings of the present invention absorbs light abruptly over a relatively narrow wavelength range. In one embodiment of the present invention the wavelength range is between approximately 400 nm and 450 nm. FIG. 3 graphically depicts a non-limiting example of an absorption spectrum for one dye used in accordance with the teachings of the present invention.

Suitable dyes are preferably biocompatible, non-polar, thermally, photochemically and hydrolytically stable. The dye also preferably has have a narrow absorption bandwidth such that it acts as a substantially vertical filter. In one embodiment the full width at half maximum (FWHM) bandwidth is less than 100 nm, in a preferred embodiment the absorption band width is less than 75 nm and in an even more preferred embodiment the FWHM bandwidth is less than 50 nm.

The dyes used in accordance with the teachings of the present invention are capable of being functionalized to allow for polymerization with the structural polymers of the lens. In one embodiment the dye is acrylate functionalized. This is particularly beneficial because functionalized dyes can be chemically bonded to the ophthalmic device polymer so that the lens is colorfast and the dye is non-extractable (i.e. will not bleed or leach out of the lens). However, it is not essential that the dye be polymerizable or capable of bonding to the ophthalmic device polymer.

In one embodiment of the present invention the dye is an Eastman Chemical yellow dye designated as Eastman Yellow 035-MA. The empirical formula of this dye is $C_{20}H_{25}N_3O_5S$ and its structure is shown below as structure 1.

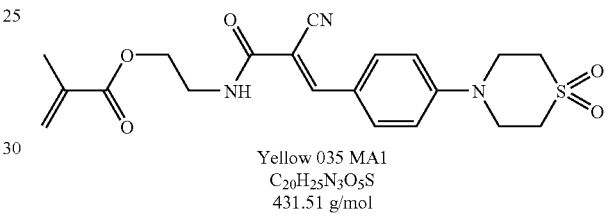

Yellow 035 MA1
$C_{20}H_{25}N_3O_5S$
431.51 g/mol

This dye is a methine dye having the absorption spectrum depicted in FIG. 3. In one embodiment the dye is functionalized with methacrylate groups and is present in the finished ophthalmic device at a concentration of between approximately 0.005% to 0.2% (w/w), preferably between approximately 0.01% to 0.1% (w/w); the structural polymer, UV absorbing dye, solvents and other biocompatible excipients making up the remaining lens composition.

The ophthalmic devices according to the present invention may be made from biocompatible polymers and include, without limitation, poly(methylmethacrylate) (PMMA). Additional polymers may be used when made using monomers selected from the non-limiting group consisting of phenylethylacrylate (PEA), phenylethylmethacrylate (PEMA), methylphenylacrylates, methylphenylmethacrylates, 2-hydroxyethyl methacrylate (HEMA). Moreover, heterocyclic N-vinyl compounds containing carbonyl functionality adjacent to the nitrogen in the ring, and particular N-vinyl lactams such as N-vinyl pryrolidone are also suitable for use in accordance with the teachings of the present invention. Moreover, the ophthalmic devices of the present invention may also be cross-linked using di- or multi-functional monomers and in small amounts as is well known in the art. Representative crosslinking agents include ethylene glycol dimethacrylate, triethylene, glycol dimethacrylate and trimethylolpropane trimethacrylate. The crosslinking agents are typically dimethacrylates or diacrylates, although dimethacrylamides are also known. Additional suitable lens-forming monomers for use in the present invention include listed at column 7, line 63 through column 8 line 40 of U.S. Pat. No. 5,662,707, the contents of which is herein incorporated by reference. See also U.S. Pat. No. 5,269,813 column 2 line 14 through column 7 line 52, specifically Table 1, this US patent is also incorporated by reference both in its entirety and as specifically cited.

The ophthalmic devices of the present invention may also contain at least one near-ultraviolet (UV) light absorbing compound such as benzophenones and benzotriazoles. Suitable examples can be found in U.S. Pat. No. 4,716,234 (specifically see column 3 line 67 through column 10 line 24); U.S. Pat. No. 4,963,160 (specifically column 2 line 61 through column 4 line 19); U.S. Pat. No. 5,657,726 (specifically column 2 line 36 through column 4 line 67) and U.S. Pat. No. 6,244,707 (specifically column 3 line 50 through column 6 line 37) the entire contents of which, specifically the cited columns numbers and lines, are herein incorporated by reference.

The ophthalmic devices of the present invention reduce the impact on scotopic vision by substantially not blocking light above 500 nm, absorbing primarily violet and ultraviolet light. The ophthalmic devices also provides retinal protection, by blocking all UV light and selectively filter some blue and violet light up to approximately 450 nm.

Figure 1:
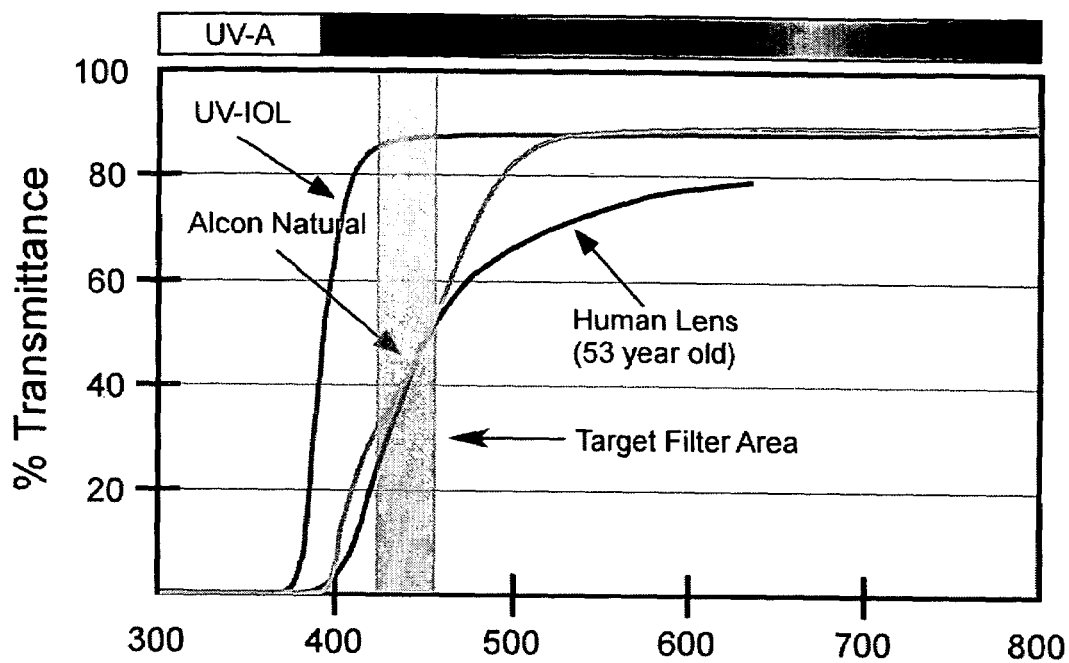
FIG. 1 graphically compares the visible light transmittance curves of an aging natural crystalline lens with a lens containing UV absorbing dyes only (UV-IOL) and a lens containing UV absorbing dyes and conventional violet light absorbing dyes (Alcon Natural). The target filter area for a vertical violet light cut-off filter made in accordance with the teachings of the present invention is depicted in yellow.

FIG. 1 compares the naturally aging human crystalline lens (the black line) with a state-of-the-art ophthalmic device (Alcon Natural) containing a violet light blocking dye (an Azo-class dye) (yellow line) demonstrating a significant drop in light transmittance for light in the blue wavelength range (between about 440 nm and 500 nm). The blue line depicts an ophthalmic device containing UV absorbing dyes but no violet-light absorbing dyes (UV-IOL). Note that both the commercial ophthalmic device and the natural human lens show a significant drop in transmittance between 400 nm and 550 nm as compared to the ophthalmic device lacking a violet blocking dye. When FIG. 1 is compared to FIG. 5, it is clear that both the natural lens and the commercial lens containing a violet blocking dye would filter wavelengths essential for optimum scotopic vision. However, is also clear that a lens lacking any violet light blocking dye or pigmentation such as the UV-ophthalmic device in FIG. 1 would expose the retina to damaging blue and violet light wavelengths. However, a lens having a violet light absorbing dye that restricted light absorption in the yellow area depicted in FIGS. 1 and 5 would both reduce blue/violet light-induced phototoxicity and improve scotopic vision compared to prior art blue blocking filters.

Figure 5:
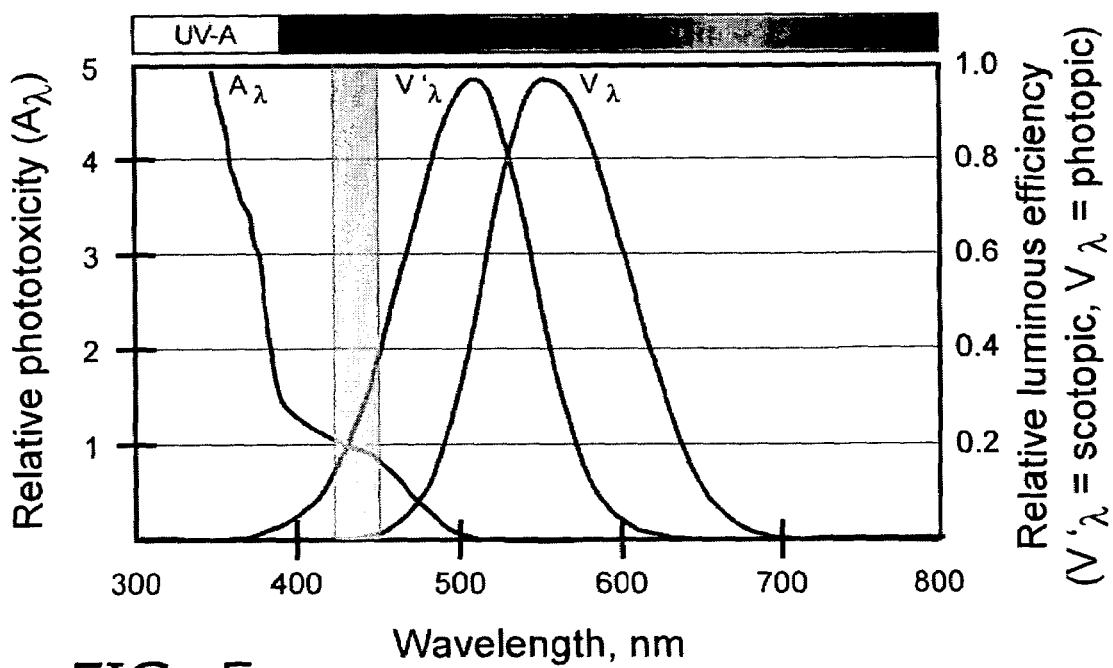
FIG. 5 graphically depicts relative phototoxicity versus wavelength in nm and relative luminous (scotopic versus photopic) efficiency as a function of wavelength in nm.

FIG. 5 graphically depicts the non-limiting theory behind the present invention. Curve $A_\lambda$ depicts retinal damage as a function of wavelength. As shown in FIG. 5 the retinal damage potential (phototoxicity) is inversely related to the wave length of light. That is, the potential for retinal damage increases as the wavelength of light decreases. Curve $V\bullet_\lambda$ depicts relative luminous efficiency for scotopic vision. As can be seen from curve $V\bullet_\lambda$ scotopic vision luminous efficiency peaks at approximately 515 nm. Curve $V_\lambda$ demonstrates that photopic vision peaks at approximately 550 nm. The area depicted in yellow in FIG. 5 represents a preferred ideal wavelength range (approximately 400 nm to 450 nm) for the violet-light vertical cut-off filter of the present invention. The violet-light vertical cut-off filter region of the present invention depicted in FIG. 5 reduces blue/violet light-induced phototoxicity while also reducing interference with violet light wavelengths essential for optimum scotopic vision. Thus an ophthalmic device having at least one light absorbing dye used to form a violet-light vertical cut-off filter according to the present invention is preferably restricted to the wavelengths as depicted in FIG. 2 and would strike a compromise between retinal protection and scotopic vision. It is understood that such an ideal ophthalmic device would also contain UV absorbing dyes that would prevent UV-induced phototoxicity as well.

Figure 7:
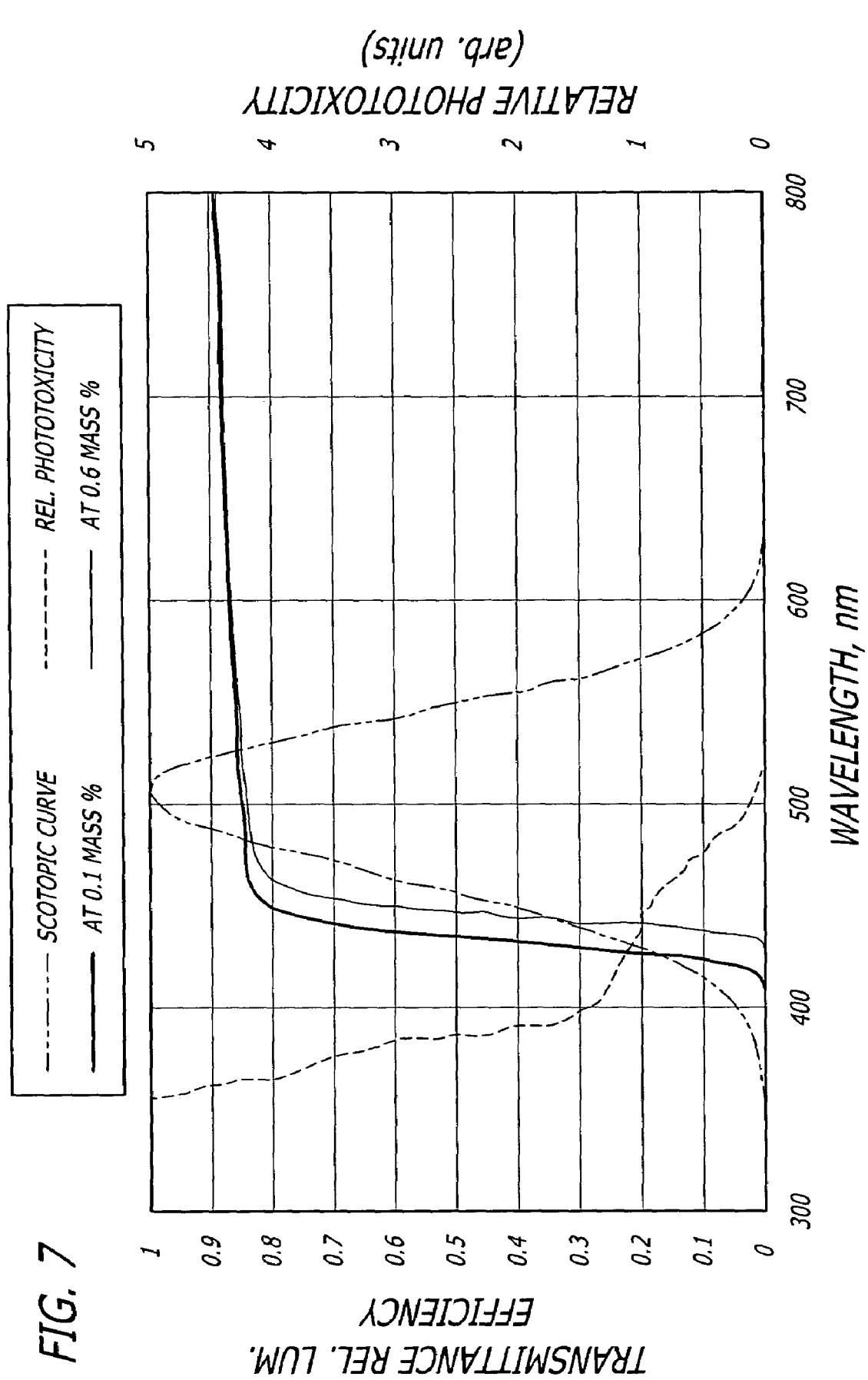
FIG. 7 is essentially a composite of FIG. 2 and FIG. 5.

FIG. 7 (FIG. 7 is essentially a composite of FIGS. 2 and 5) demonstrates two aspects of the present invention. First the curve gradients (slopes) are extremely steep thus narrowing the range of wavelengths affected by the light absorbing dye. Secondly, FIG. 7 demonstrates that wavelength absorption curve gradient should be relatively independent of dye concentration. However, changes in dye concentration can slightly effect wavelength spread (compare the origins of 0.1% dye mass to the 0.6% dye mass along the X-axis). This is especially important because conventional ophthalmic devices have the dye dispersed uniformly throughout the structural polymer. Thus as lens thickness is modified to change diopter, dye concentration changes. Consequently, if the curve gradient were excessively dye-concentration dependent, scoptoic vision and retinal protection characteristics of the ophthalmic device would vary significantly with diopter.

Figure 4:
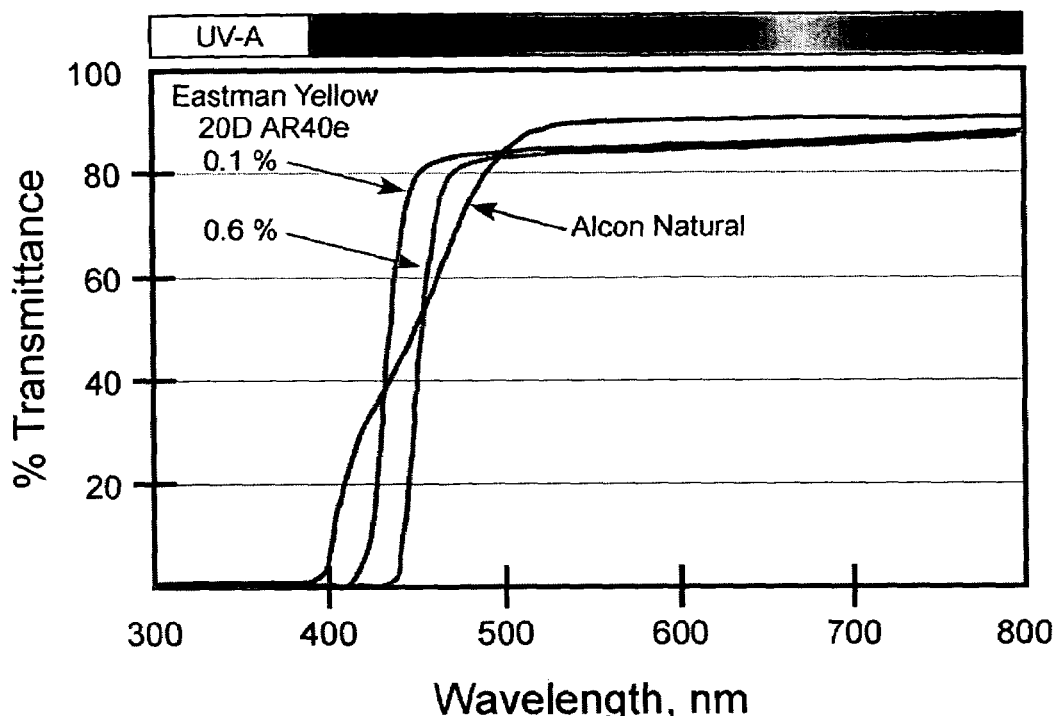
FIG. 4 graphically depicts the idealized filter range (area between the red curves) for the violet light vertical cut-off filter made in accordance with the teachings of the present invention compared to the state-of-the-art ophthalmic device (Alcon Natural, blue curve).

However, FIG. 2 demonstrates that a ten-fold change in dye concentration, when used in accordance with the teachings of the present invention, only slightly shifts the wavelength absorption spread and has virtually no impact on curve gradient. Furthermore, FIG. 4 illustrates that for a fixed diopter (20D) lens, a six-fold increase in dye concentration change results in a consistent curve gradient and relatively little shift in wavelength absorption characteristics. Thus while it may be possible to adjust, or fine tune, the wavelength absorption range by varying dye concentration, the steepness of the curve gradient remains constant and thus acts as a vertical cut-off filter in accordance with the teachings herein.

Figure 6:
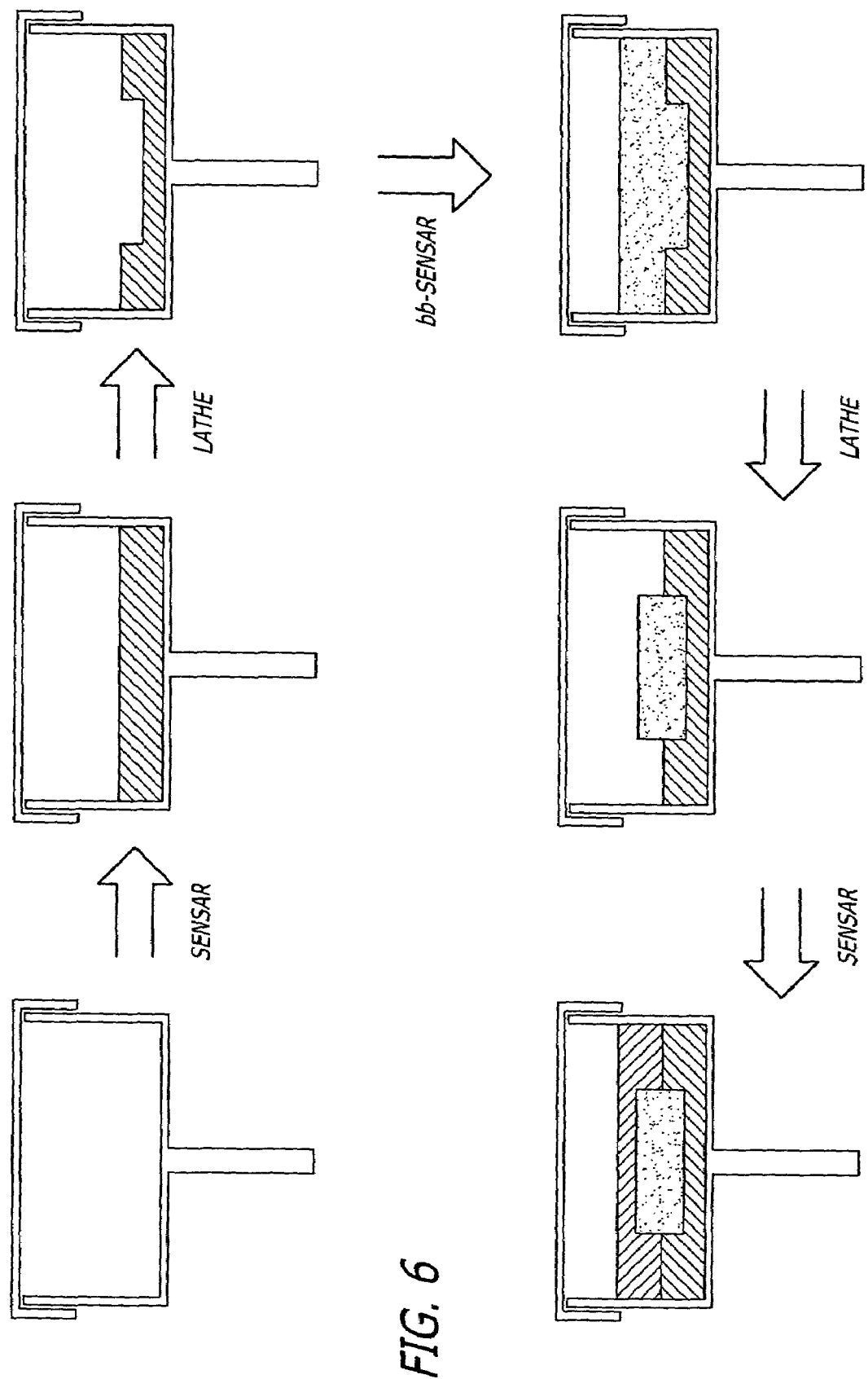
FIG. 6 depicts an embodiment of the present invention wherein the dye used to form the vertical violet light cut-off filter is localized to a core within a composite button that comprises the ophthalmic device FIG. 7 graphically depicts the violet light vertical cut-off filter made in accordance with the teachings of the present invention as applied to relative phototoxicity as a function of light wavelength overlaid against the scotopic vision curve.

In another embodiment of the present invention depicted in FIG. 6 the dye concentration remains constant regardless of lens thickness, and hence diopter, by localizing the dye with is a central core. Thus, as the lens is shaved to adjust diopter, only the non-dye containing polymer is removed and thus the violet light absorbing characteristics remain constant. The lens design in FIG. 6 has the added advantage of localizing the dye to the pupil area of the lens. Thus under bright light conditions when blue/violet light exclusion is necessary to reduce blue/violet dye-associated phototoxicity the constricted pupil is completely within the dye containing zone of the ophthalmic device. However, under dim light conditions where maximum violet light penetration is necessary for optimum scotopic vision the dilated pupil receives both filtered and unfiltered light. This is discussed more fully in U.S. utility application Ser. No. 11/027,876.

In one embodiment of the present invention ophthalmic devices are provided having at least one violet light absorbing dye with an absorption profile essentially the same as that depicted in FIG. 3. The violet light absorbing dyes are generally biocompatible, non-polar and capable of being functionalized such that they can be polymerized with the ophthalmic device structural polymers. In one embodiment of the present invention violet-light absorbing dyes having a methine linkage are used. Light absorbing dyes having methine linkages are described in U.S. Pat. No. 5,376,650 issued Dec. 27, 1994 the entire contents of which is herein incorporated by reference in its entirety.

In one embodiment of the present invention the dye is an Eastman Chemical yellow dye designated as Eastman Yellow 035-MA. This dye is a methine dye having the absorption spectrum depicted in FIG. 3. In one embodiment the dye is functionalized with methacrylate groups and is present in the finished ophthalmic device at a concentration of between approximately 0.005% to 0.2% (w/w), preferably between approximately 0.01% to 0.1% (w/w); the structural polymer, UV absorbing dye, solvents making and other biocompatible excipients making up the remaining lens composition.

The ophthalmic devices made in accordance with the teachings of the present invention have a violet-light vertical cut-off filter incorporated therein wherein the violet-light vertical cut-off filter abruptly absorbs light between the wavelengths of between approximately 400 nm and 450 nm (see FIG. 2). Moreover, the wavelength spread and curve gradient, or slope, is within the parameters depicted in FIGS. 2 and 5 as depicted in yellow. However, it is understood that the wavelength absorption range can extend to 400 nm at the low end and 450 nm at the high end providing the curve gradient remains as depicted in FIG. 2.

In another embodiment an ophthalmic device is provided having a violet-light vertical cut-off filter as described above wherein the ophthalmic device has the structural characteristics depicted in FIG. 6. In this embodiment the violet light absorbing dye may or may not be functionalized and may or may not be co-polymerized with the structural polymer.

While this invention has been described with reference to preferred embodiments thereof, these are by way of illustration and not limitation. Variations and modifications thereon can be made by those skilled in the art without departing from the scope or spirit of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An ophthalmic device, comprising:
    a body having a center aperture for transmitting light onto the retina of an eye;
    a dye disposed within at least a portion of said aperture;
    said center aperture having a first transmittance of approximately 10 percent at a first wavelength that is between 420 nm and 450 nm;
    said center aperture having a second transmittance at a second wavelength that is about 10 nm greater than said first wavelength, said second transmittance being about 50 percent.

2. An ophthalmic device according to claim 1, wherein said ophthalmic device has substantially no optical power.

3. An ophthalmic device according to claim 1, wherein said ophthalmic device is a lens.

4. An ophthalmic device according to claim 1, wherein said ophthalmic device is an intraocular lens.

5. An ophthalmic device according to claim 1, wherein said ophthalmic device is a contact lens.

6. An ophthalmic device according to claim 1, wherein said ophthalmic device is a spectacle.

7. An ophthalmic device according to claim 1, wherein said first wavelength is between about 420 nm and about 440 nm.

8. An ophthalmic device according to claim 1, wherein said first wavelength is about 430 nm and said second wavelength is about 440 nm.

9. An ophthalmic device according to claim 1, wherein said first wavelength is about 424 nm and said second wavelength is about 435 nm.

10. An ophthalmic device according to claim 1, wherein said first wavelength is about 439 nm and said second wavelength is about 448 nm.

11. An ophthalmic element, comprising:
 a body having a center aperture for transmitting light onto the retina of an eye;
 a dye disposed within at least a portion of said aperture;
 said center aperture characterized by a transmittance function over a wavelength range between 420 nm and 450 nm;
 said transmittance function having a slope over at least a portion of the wavelength range that is greater than about 3 percent change in transmittance per nanometer change in wavelength.

12. An ophthalmic element according to claim 11, wherein said transmittance function has a slope over at least a portion of the wavelength range that is greater than about 4 percent change in transmittance per nanometer change in wavelength.

\* \* \* \* \*